United States Patent [19]
Rello et al.

[11] Patent Number: 5,487,388
[45] Date of Patent: Jan. 30, 1996

[54] THREE DIMENSIONAL ULTRASONIC SCANNING DEVICES AND TECHNIQUES

[75] Inventors: Michael J. Rello, Harleysville; Richard M. Derman, Newtown, both of Pa.

[73] Assignee: Interspec. Inc., Ambler, Pa.

[21] Appl. No.: 333,096

[22] Filed: Nov. 1, 1994

[51] Int. Cl.⁶ ................................................ A61B 8/00
[52] U.S. Cl. ................................ 128/660.09; 128/916
[58] Field of Search .................. 128/660.07, 660.08, 128/660.09, 660.10, 662.06; 73/633

[56] References Cited

U.S. PATENT DOCUMENTS

| | | | |
|---|---|---|---|
| 4,167,180 | 9/1979 | Kossoff | 128/660.09 |
| 4,272,991 | 6/1981 | Cribbs | 128/660.09 X |
| 4,341,120 | 7/1982 | Anderson | 73/618 |
| 4,637,256 | 1/1987 | Sugiyama et al. | 73/633 |
| 4,747,411 | 5/1988 | Ledley | 364/414 X |
| 4,932,414 | 6/1990 | Coleman et al. | 128/660.09 |
| 5,078,145 | 1/1992 | Furuhata | 128/916 |
| 5,152,294 | 10/1992 | Mochizuki et al. | 128/662.03 |
| 5,159,931 | 11/1992 | Pini | 128/660.07 |
| 5,167,165 | 12/1992 | Brucher et al. | 128/660.07 |
| 5,331,962 | 7/1994 | Coleman et al. | 128/660.09 |
| 5,353,354 | 10/1994 | Keller et al. | 382/6 |

OTHER PUBLICATIONS

"Three-dimensional Reconstruction of Echocardiograms Based on Orthogonal Sections", S. Tamura, Patt. Recog. v 18, No. 2, pp. 115–124 (1985).

"Multidimensional Ultrasonic Imaging for Cardiology", H. McCann et al. Proc. IEEE, v 76, No. 9, pp. 1063–1073 (Sep. 1988).

Tomtec GmbH D-85386 Eching Sweep Device (3 photographs).

*Primary Examiner*—Francis Jaworski
*Attorney, Agent, or Firm*—W. Brinton Yorks, Jr.

[57] ABSTRACT

A method and device for three dimensional ultrasonic scanning of a patient is described by which an ultrasonic probe scans image planes oriented in a wedge or fan shaped volume. The probe is moved in an arc of travel about an apex which is below the scanning device and may be adjustably located within the probe or lower, such as between the ribs of the patient. The inventive method and device enable a significant volume of the heart to be scanned intercostally and viewed in a three dimensional image format.

15 Claims, 6 Drawing Sheets

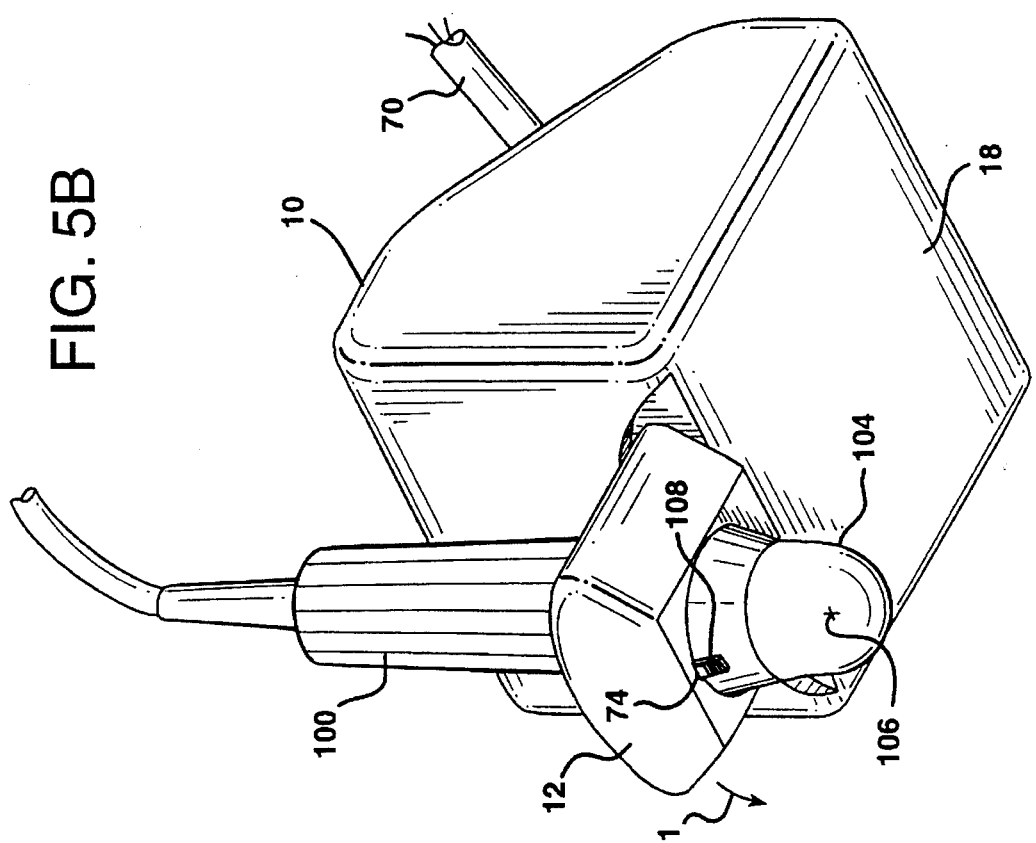
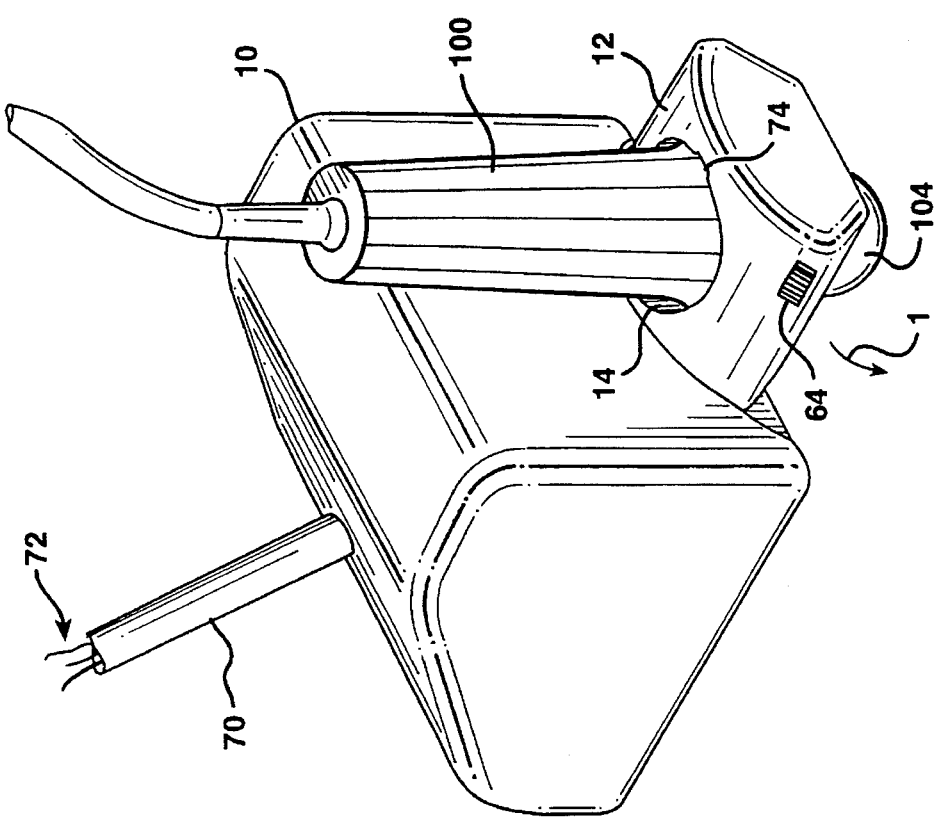

THREE DIMENSIONAL ULTRASONIC SCANNING DEVICES AND TECHNIQUES

This invention relates to devices for ultrasonically scanning and displaying a three dimensional volume, and in particular to ultrasonic scanning devices which acquire volumetric ultrasonic data over a wedge shaped volume of a subject.

Various methods and devices have been proposed for ultrasonically scanning a volume within a subject for three dimensional analysis and display. Many of these techniques involve the scanning of a number of spatially adjacent image planes. The ultrasonic information from these associated planes can be analyzed and displayed on the basis of spatial coordinates of the data within a plane, and on the basis of the spatial relationship of each plane to the others. The information can be displayed in a three dimensional image format such as a perspective view of the volume being imaged.

A number of scanning techniques have been proposed for acquiring these spatially related image planes. U.S. Pat. No. 5,353,354, for instance, proposes acquiring and displaying a number of parallel image planes, and a technique for displaying two intersecting image planes. U.S. Pat. No. 5,159,931 proposes acquiring and displaying a number of angularly related image planes which intersect at a common axis. The present invention describes another technique, which is to acquire a number of image planes arranged in a fan shaped wedge, with the apex of the wedge located toward the ultrasonic probe.

The fan shaped scanning technique of the present invention has been found to be well suited to cardiac scanning, where the heart is being scanned intercostally, or through the ribs. Since ultrasonic energy does not transmit efficiently through bone and cartilage, the ultrasonic energy must be transmitted and received through the small apertures between the ribs. This does not present a significant difficulty when a single plane is scanned. Under these conditions the ultrasonic probe can be held at the desired angle to intersect the heart while transmitting and receiving ultrasonic energy between the ribs. However, when a plurality of spatially associated image planes are to be acquired intercostally, the small aperture between the ribs is an impediment to moving the scan plane over the desired volume of the heart without intersecting the ribs. The techniques of the aforementioned patents cannot be used to image the heart efficiently through the ribs, as the rib aperture is too small to permit scanning as described in those patents without interference from the ribcage.

In accordance with the principles of the present invention, a three dimensional ultrasonic scanning technique and a device suitable for performing the technique are described. The inventive technique is to sweep an ultrasonic probe in an arcuate manner so as to scan planes which are spatially oriented in a fan or wedge shape. In a preferred embodiment the apex of the scan volume wedge is just above the point of contact of the ultrasonic probe and the surface of the subject, enabling the intercostal scanning of a wide volume inside the body of a patient. A novel device is described for performing the inventive technique, which locates the apex of the scan volume wedge below the lower surface of the device. Through adjustment of the position of an ultrasonic probe in the device, the apex can be located just above the skin line of the patient, or even between the ribs themselves.

Figure 2:
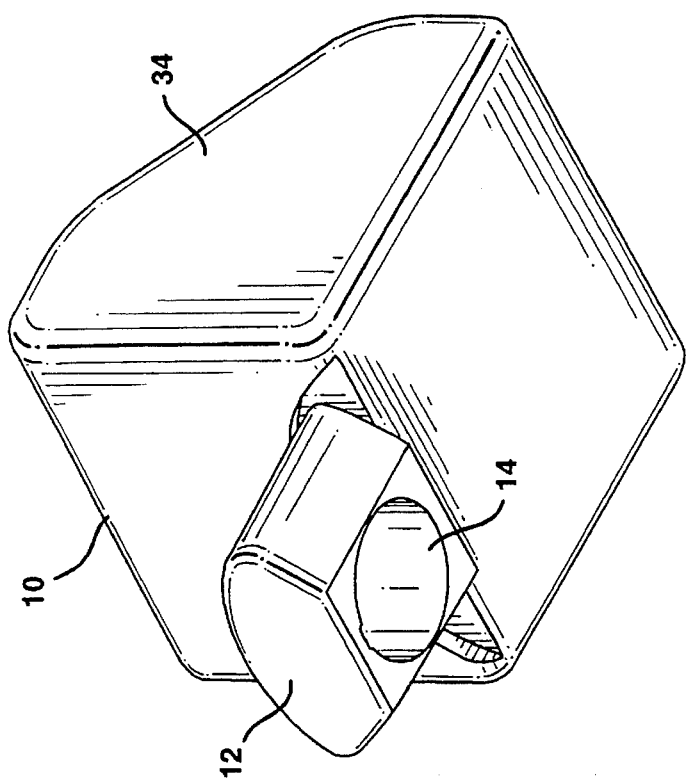
FIG. 2 is a lower perspective view of the ultrasonic scanning device of FIG. 1.
Figure 1:
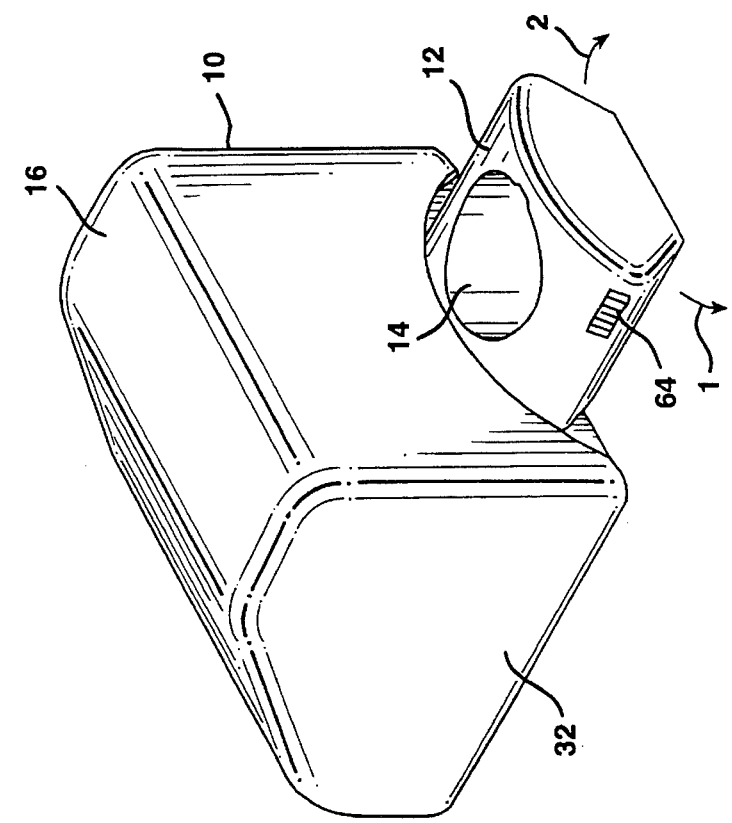
FIG. 1 is a top perspective view of an ultrasonic scanning device constructed in accordance with the principles of the present invention.
Figure 6B:
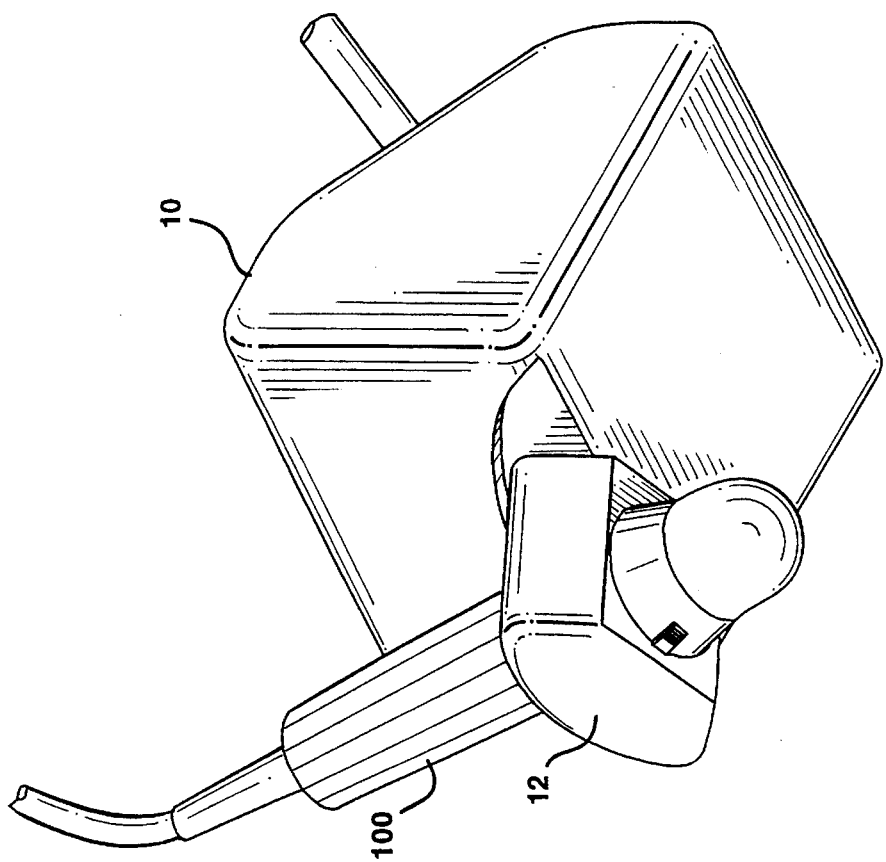
Figure 6A:
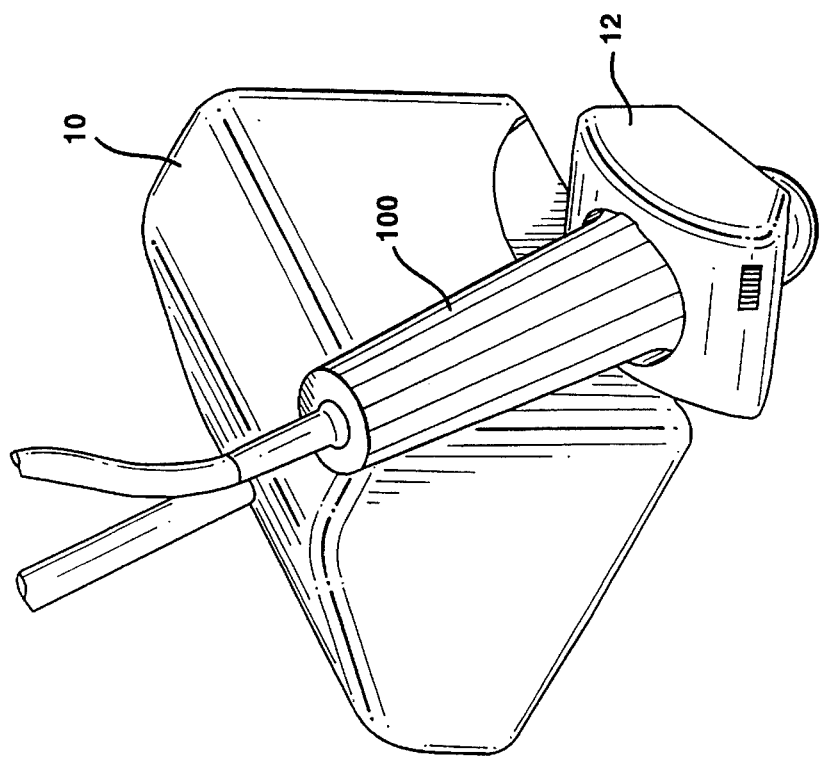

FIGS. 5a and 5b illustrate the mounting of an ultrasonic probe in the ultrasonic scanning device of FIGS. 1 and 2; and FIGS. 6a and 6b illustrate the scanning technique of the present invention by use of the ultrasonic scanning device and probe of FIGS. 5a and 5b.

Referring first to FIGS. 1 and 2, two perspective views of an ultrasonic probe scanning device constructed in accordance with the principles of the present invention are shown. The scanning device includes a main housing 10 and a probe cradle 12. An ultrasonic probe fits into a hole 14 in the probe cradle and is clamped in place by moving a clamp lock switch 64. The probe cradle is detachable from the housing, allowing different cradles with holes for ultrasonic probes of different shapes and sizes to be used. The probe cradle 12 is rocked in an arcuate motion, indicated by motion arrows 1 and 2, by the drive mechanism contained in the main housing 10.

The scanning motion developed by the scanning device may be appreciated with reference to FIGS. 3a–3e. In these drawings an ultrasonic probe 100 is shown clamped in a probe cradle 12. The probe shown is a mechanically oscillated probe in which an ultrasonic transducer 102 is moved back and forth inside the dome shaped, fluid filled lens cap 104, but the invention is applicable to other types of probes as well. The path of motion of the transducer is orthogonal to the plane of the drawing. Thus, the scan plane over which the transducer transmits and receives ultrasonic energy is also orthogonal to the plane of the drawing and is shown edge-on by the scan plane representation 30.

The drive mechanism of the scanning device is pivotally connected to the probe cradle 12. The probe cradle is connected at the ends of two connecting rods 24 and 26. The connecting rods 24 and 26 are pivotally connected to two triangular crankshafts, an upper crankshaft 20 and a lower crankshaft 22. Each crankshaft has a drive shaft fastened in a hole 28, 29 to move the crankshafts. The triangular cranks 20, 22 move in planes parallel to the plane of the drawing. Since the cranks move about the positionally fixed shafts, they will move about a reference line 50, which is a common reference from one drawing to the next.

When the crankshafts are in the positions shown in FIG. 3a the probe cradle 12 and probe 100 are seen to be sharply inclined with respect to the reference line 50. This causes the scan plane 30a to be sharply inclined also. As the crankshafts begin to move clockwise about their pivot points 28, 29 the inclination of the probe cradle, probe and scan plane is lessened as FIG. 3b shows. As the clockwise motion of the crankshafts continues the probe and scan plane 30c will reach a vertical alignment with the reference plane as shown in FIG. 3c. The motion continues to incline the probe to the other side of the vertical position as shown by FIG. 3d and then FIG. 3e. The motion of the drive mechanism is then reversed, causing the probe cradle and probe to traverse back through their inclined and vertical positions until they return to the position of FIG. 3a.

A "+" mark identified by reference numeral 106 is drawn in the dome shaped lens cap 104 of the probe in each figure. It is seen that the + mark is always located on the reference line 50. Hence this reference mark, located at approximately the center of the hemispherical dome, is the apex of the wedge shaped volume that is traversed by the scan planes 30a–30e. If the ultrasonic probe is clamped in a higher position in the probe cradle the + mark will be located lower toward the tip of the dome, or even in front of the dome.

It has been found that scanning about the center of the hemispherical dome of the lens 104 enables the scan plane to constantly pass through a narrow aperture of the ribs as the probe is moved through its arc of travel. This scanning technique also enables a large wedge shaped volume behind the ribs to be covered by the scan planes. Thus, a significant three dimensional field of view is provided for a given aperture or window between the ribs, enabling three dimensional scanning and imaging of the heart. For a very narrow rib aperture the ultrasonic probe can be clamped further up in the probe cradle, thereby located the + mark apex at the skin surface or even between the ribs of the patient.

Figure 3:
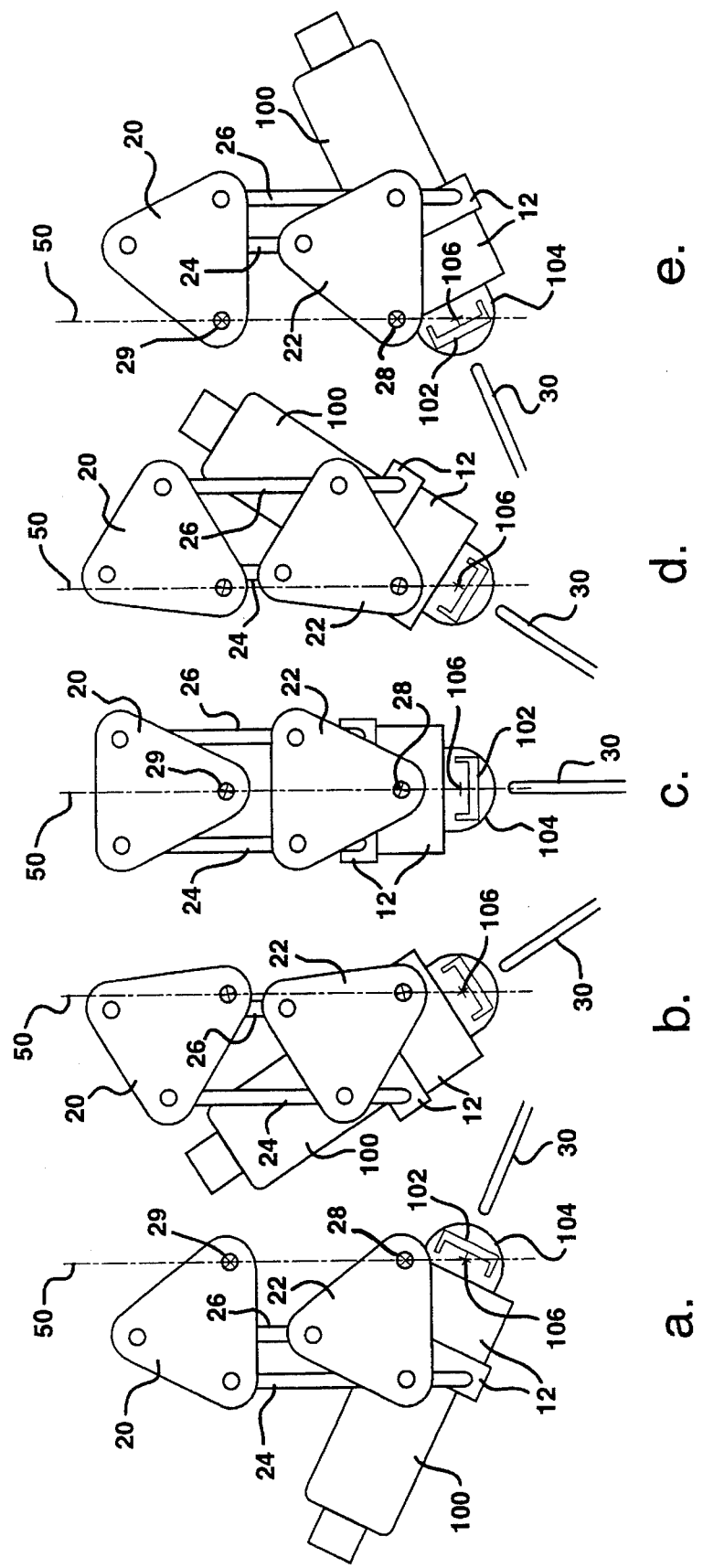
FIGS. 3(a–e) illustrate the principles of operation of the scanning device of the present invention and also the performance of the scanning technique of the present invention.

It will be appreciated that the scanning motion depicted in FIG. 3 will not roll the dome shaped probe lens 104 back and forth like a ball, but will effect a slight sliding of the lens 104 against the skin of the patient. This slight sliding is facilitated by the ultrasonic gel couplant applied to the lens and the patient for ultrasonic scanning.

FIGS. 4a–4d illustrate the drive mechanism of the main housing 10. In these figures the upper housing cover 16 has been removed. One or both of the housing side covers 32, 34 (also shown in FIGS. 1 and 2) remain in the FIG. 4 drawings for orientation reference.

Figure 4A:
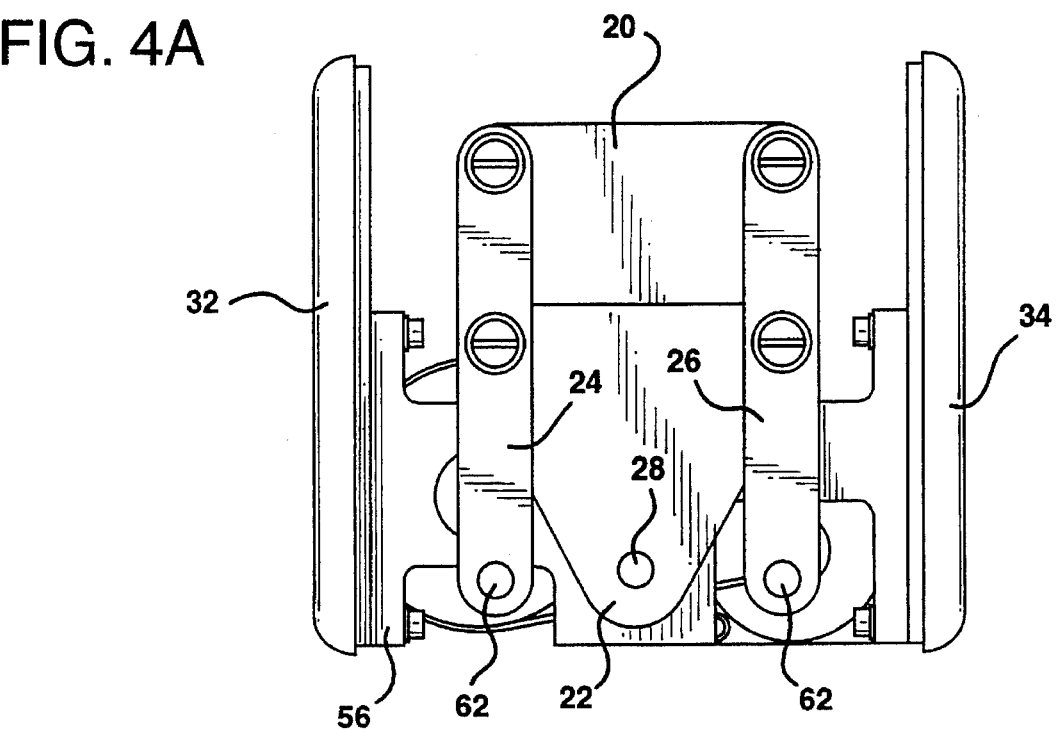
FIGS. 4a–4d are interior views of the ultrasonic scanning device of FIGS. 1 and 2.

In FIG. 4a the mechanism of the main housing is viewed from the front, the side to which the probe cradle 12 is attached. The probe cradle is attached to two rods 62 extending from holes at the ends of the connecting rods 24 and 26. It will be appreciated that the connecting rods can be made as long as desired to extend the rods 62 and hence the probe cradle further below the bottom of the main housing 10. The connecting rods are connected by screws to the lower crankshaft 22 and the upper crankshaft 20.

Figure 4B:
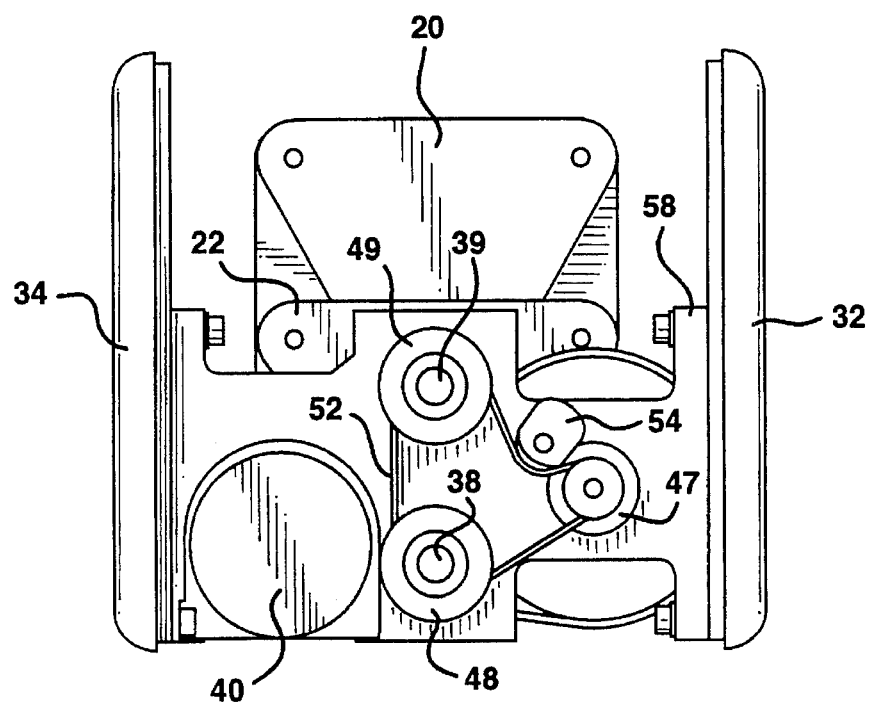
Figure 4C:
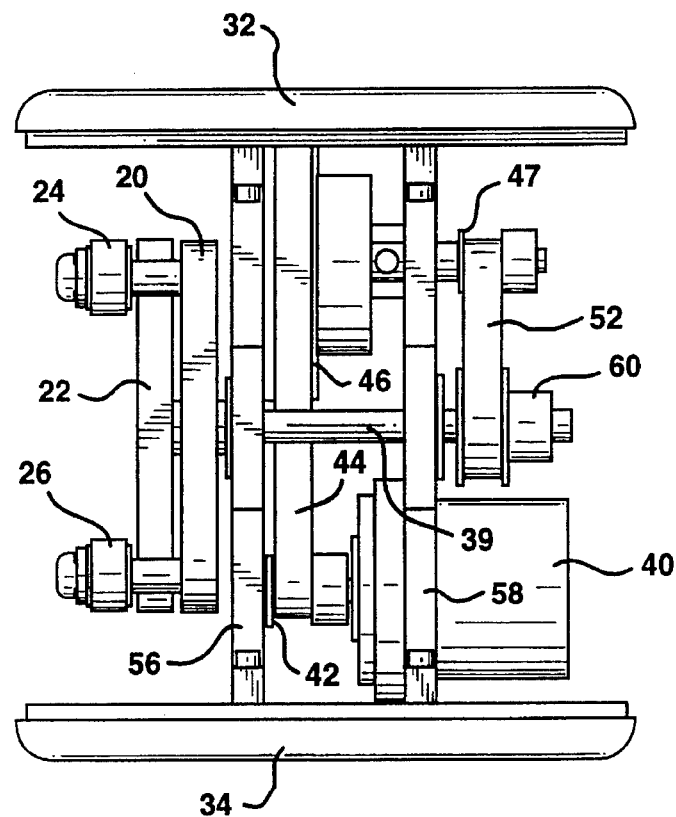
Figure 4D:
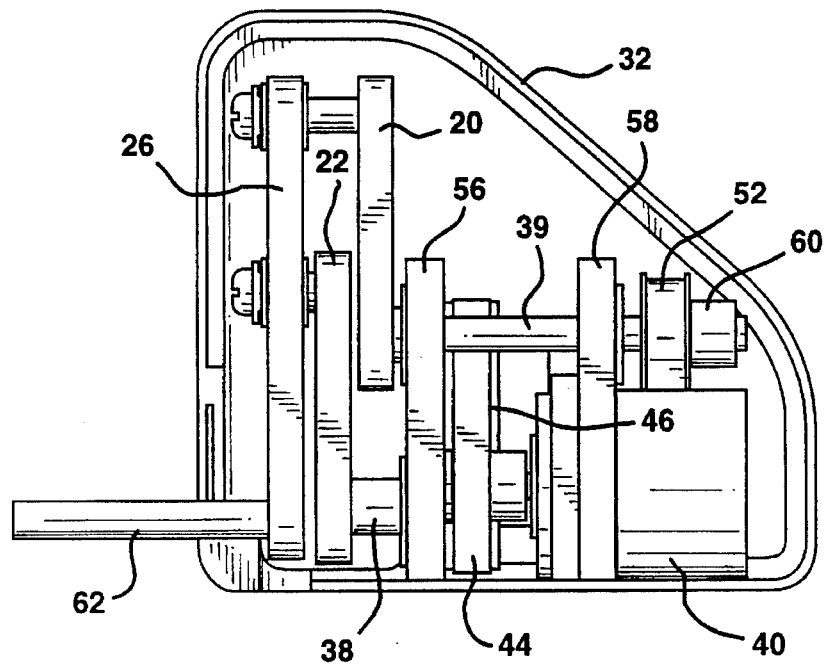

FIGS. 4c and 4d show the interior of the main housing from the top and side, respectively. The drive shaft 39 of the upper crankshaft is fastened in the hole 29 of the crank 20 and extends through bearings in a front plate 56 and a rear plate 58 to the rear of the main housing. An end stop detector 60 is located at the end of the drive shaft 39 and optically detects when the shaft has been rotated to either of the limits of its range of rotation. This affords the ability to calibrate the position of the mechanism and also provides an element of safety. The end stop detector can be an optical device, a magnetic device or a mechanical device as desired. The drive shaft 38 of the lower crankshaft is fastened in the hole 28 of the crank and similarly extends through bearings in the front and rear plates to the rear of the main housing. The rotation of the drive shaft 38 also is monitored by an end stop detector at the rear of the shaft.

The drive shafts 38, 39 are driven by a motor 40. In a constructed embodiment an open loop controlled stepper motor was used, but a closed loop controlled DC or stepper motor with a position encoder can also be employed. Each step of the stepper motor increments the scan plane to another position within the volume being scanned. A pulley 42 is connected to the shaft of the motor. A front timing belt 44 is used to drive a large transmission pulley 46 from the motor pulley 42. The large transmission pulley 46 is connected by a shaft extending through bearings in the front and rear plates to a small transmission pulley 47 in a jack shaft arrangement. This transmission configuration results in a rotational reduction that affords significant torque drive for the crankshafts. The rear view of FIG. 4b illustrates a rear timing belt looped around the small transmission pulley 47, a pulley 48 on the lower crankshaft 38 and a pulley 49 on the upper crankshaft 39 to drive these shafts. An idler 54 maintains the desired tension on the rear timing belt. Thus it is seen that the motor drive is reduced to a lower drive ratio and applied to the drive shafts of both of the crankshafts to rotate them back and forth. The motor may be stepped in one direction, rotating the shafts 38, 39 and incrementally moving the probe cradle in one direction of its arc of travel. The end stop detectors are used during calibration to signal the range of travel limits to the controlling system. During actual ultrasound data acquisition, the image plane is stepped through any desired angle within these limits.

This scanning motion may be appreciated with reference to FIGS. 5a, 5b, 6a and 6b, which show the main housing and probe cradle of FIGS. 1 and 2 with an ultrasonic probe 100 inserted in the probe cradle 12. The ultrasonic probe has a scan plane marker 108 on one side of the probe. This marker physically protrudes from the case of the probe and marks the side of the scan plane. The probe scan plane marker 108 engages a keyway 74 on one side of the hole 14 of the probe cradle 12. With the scan plane marker 108 so engaged in the keyway 74, the scan plane of the probe will be orthogonal to the arc of travel of the cradle, indicated by motion arrow 1. The probe 100 is inserted into the hole 14 to the desired depth, then clamped in place by the clamp lock switch 64. In a constructed embodiment a spring loaded cam and lever arrangement was used for the probe clamp, although other mechanisms may also be found to be suitable.

When the probe is clamped in the probe cradle 12 as shown in FIGS. 5a and 5b the tip of the hemispherical probe lens 104 is approximately 4 cm. below the bottom 18 of the main housing. The apex of the scan volume about which the lens rotates is also below the bottom of the housing. By keeping this center of rotation below the housing and the probe cradle better access is afforded to the patient. There is no need to rest the housing on the patient or for the patient to have any contact with the housing. This is an advantage when scanning neonatal patients, for example. In a preferred embodiment the main housing 10 is supported by a series of articulating arms 70, one of which is shown attached to the main housing 10. The articulating arms support the scanning device and also carry signal and control lines 72 to the motor 40 and detectors 60.

FIGS. 5a and 5b show the probe and probe cradle in the vertical position of FIG. 3c. When the probe cradle is moved in the direction of travel indicated by arrow 1 it can attain the position of FIG. 3b which is shown in FIGS. 6a and 6b. The crankshafts and connecting rods are pivoted to the left, swinging the probe cradle 12 in an arc to the left as shown by FIGS. 6a and 6b. As the ultrasonic probe is stepped in its arc of travel from one position to another an image plane is scanned by the probe at each position. Each step of the motor provides a position signal indicating the angular orientation of the scan plane at that time with respect to the adjacent planes, and spatial data within a scan plane is provided by the ultrasonic probe in the usual manner. This spatial and position data is recorded by the ultrasound system along with the image information and can be used to display the image information of the fan or wedge shaped scan volume in a three dimensional perspective view, a thickness view in which the scan planes overlay each other, or other three dimensional image formats. This fan or wedge shaped scanning technique has been found to be most advantageous when gathering volumetric ultrasonic image information of the heart from an ultrasonic aperture or window passing between the ribs. The inventive apparatus provides patient comfort, good acoustical contact, and a wide field of view through the ribs.

The present invention is useful in many diagnostic applications. In addition to the intercostal acquisition of cardiac data sets discussed above, the inventive technique and device have significant application in any scanning situation where there is a small aperture, or where there is some other obstacle to access. Some examples of such applications include neonatal cephalic imaging through the fontanelle, where neurologic conditions are diagnosed through the plates of the skull. Trans-orbital imaging of the eye is facilitated by this technique and device, as is imaging of the carotid artery, where the jaw can pose an obstacle to imaging above the carotid bifurcation. Furthermore, scanning by fanning the scan plane about a single point avoids the problem of anatomical irregularities which interfere with other three dimensional scanning techniques such as parallel scan plane acquisition.

What is claimed is:

1. A method for ultrasonically scanning a volumetric region within the body of a patient by means of an ultrasonic probe controlled to scan a scan plane through an acoustic cap and a device which moves said probe through an arc of travel, comprising the steps of:

locating said probe and device so that the acoustic cap of said probe is in acoustical contact with the body of the patient;

controlling said device to move said probe through an arc of travel while acquiring ultrasonic information from a plurality of scan planes occupying a wedge shaped volume having an apex which is below the surface of said device which opposes the patient;

recording the positions of said scan planes; and processing the ultrasonic information of said scan planes three dimensionally.

2. The method of claim 1, wherein said step of controlling comprises the step of controlling said device to move said probe through an arc of travel while acquiring ultrasonic information from a plurality of scan planes occupying a wedge shaped volume having an apex which is between the surface of said device which opposes the points at which said scan planes enter the body of said patient and said points.

3. The method of claim 1, wherein said step of controlling comprises the step of controlling said device to move said probe through an arc of travel while acquiring ultrasonic information from a plurality of scan planes occupying a wedge shaped volume having an apex which is in front of the surface of said device which opposes the patient and is at or beyond the points at which said scan planes enter the body of the patient.

4. The method of claim 3, wherein said step of controlling further comprises controlling said device to move said probe through an arc of travel while acquiring ultrasonic information from a plurality of scan planes occupying a wedge shaped volume having an apex which is between the ribs of the patient.

5. The method of claim 1, wherein said step of processing comprises the step of displaying a three dimensional image of said wedge shaped volume which displays a portion of said wedge shaped volume which is within the body of said patient.

6. The method of claim 1, wherein said step of controlling further comprises controlling said device to move said probe through an arc of travel which is substantially orthogonal to the scan plane of said ultrasonic probe.

7. A device for ultrasonically scanning a wedge shaped volumetric region within the body of a patient by arcuately moving an ultrasonic probe controlled to scan a scan plane over said region such that the wedge shade diverges from an apex located proximal to said probe comprising:

probe cradle means for retaining said ultrasonic probe for arcuate travel of said probe and its scan plane about a point of rotation which is in front of the nearest surface of said probe cradle means which opposes the points at which said scan planes enter the body of said patient; and motive means, coupled to said probe cradle means for moving said probe cradle means through its arc of travel, wherein said point of rotation is in front of a plane tangential to the nearest surface of said motive means which opposes the body of said patient when said probe cradle means is oriented in its arc of travel such that said tangential plane and the opposing body of said patient intersected by the scan plane are both substantially parallel and normal to the scan plane of said probe.

8. The device of claim 7, wherein said motive means comprises first and second connecting rods connected to said probe cradle means, and crankshaft means coupled to said connecting rods for rotation about a pivot point.

9. The device of claim 8, further comprising a motor connected to said pivot point of said crankshaft means.

10. The device of claim 9, further comprising a transmission coupled between said motor and said crankshaft means for increasing the torque applied to said crankshaft means from said motor.

11. The device of claim 8, wherein said crankshaft means comprises a first crankshaft coupled to said connecting rods and a second crankshaft coupled to said connecting rods, each of said crankshafts having a shaft connected at a pivot point.

12. The device of claim 11, wherein said crankshaft pivot points and said point of rotation are aligned in a line.

13. The device of claim 7, wherein said probe cradle means includes a keyway for retaining said ultrasonic probe in a predetermined orientation with respect to said arc of travel.

14. The device of claim 7, further comprising adjustable retaining means for adjusting the position of said ultrasonic probe with respect to said point of rotation.

15. The device of claim 7, further comprising support means coupled to said motive means for supporting said probe cradle means and said motive means away from the surface of the body of a patient.

* * * * *